US005578799A

United States Patent [19]
Callahan et al.

[11] Patent Number: 5,578,799
[45] Date of Patent: Nov. 26, 1996

[54] PATIENT-TO-TRANSDUCER INTERFACE DEVICE

[75] Inventors: Thomas F. Callahan, Maynard; Matthew G. Callahan, Ipswich, both of Mass.; Ann F. Bell, Kenosha, Wis.

[73] Assignee: University Research Engineers & Ass., Maynard, Mass.

[21] Appl. No.: 458,125

[22] Filed: Jun. 2, 1995

[51] Int. Cl.$^6$ .................................................. H04R 25/00
[52] U.S. Cl. ............................................................ 181/137
[58] Field of Search ...................................... 181/131, 137; 381/67; 128/715

[56] References Cited

U.S. PATENT DOCUMENTS

| | | | |
|---|---|---|---|
| 3,867,925 | 2/1975 | Ersek | 181/131 X |
| 4,867,265 | 9/1989 | Wright | 181/131 |
| 4,995,473 | 2/1991 | Packard | 181/137 |
| 5,467,775 | 11/1995 | Callahan et al. | 128/715 |

*Primary Examiner*—Khanh Dang
*Attorney, Agent, or Firm*—Lynn Fiorito Watts

[57] ABSTRACT

A disposable patient-to-transducer interface device for use in securely holding a transducer such as a stethoscope head positioned against the skin surface of a patient. The interface device may be adhered to the patient's skin surface and the stethoscope head securely received in an opening provided in the device. When in use, the interface device substantially surrounds the stethoscope head thereby providing a passive barrier to ambient noise. The interface device also develops a relatively good air seal around the stethoscope head and thus provides an additional barrier to ambient noise. Furthermore, the interface device prevents substantial movement of the transducer head and, thereby, minimizes the amount of surface motion noise generated and detected by the transducer head. In addition, when the interface device is attached to the skin surface of the patient, it establishes a good reference point whereby continual or periodic monitoring of a particular location on the patient may be accomplished.

19 Claims, 2 Drawing Sheets

5,578,799

PATIENT-TO-TRANSDUCER INTERFACE DEVICE

The present invention was made with U.S. Government support, and the U.S. Government has certain rights in the invention.

BACKGROUND OF THE INVENTION

The present invention relates to an interface device that is used as an interface or interconnection between a patient and a transducer mechanism in order to hold the transducer mechanism securely against the skin surface of the patient at a fixed location.

When detecting and listening to various patient body sounds such as cardiac, pulmonary and Korotkoff sounds, a doctor, nurse, or technician oftentimes uses a transducer mechanism such as a stethoscope having a stethoscope head. The stethoscope head is normally placed against the skin surface of the patient in order to detect the body sounds. The stethoscope, however, in addition to detecting the body sounds may also detect undesirable airborne noise and surface motion noise. The airborne noise includes surrounding ambient noise that may be transmitted through the stethoscope head and detected by the listener. The surface motion noise can occur when the stethoscope head moves over or along the skin surface of the patient. Even a slight motion of the stethoscope head over the skin surface can cause unwanted noise. Such undesirable airborne and surface motion noise can interfere with the user's ability to properly discern and hear the body sounds. An object of the present invention, therefore, is to provide an interface device that can provide a passive noise barrier against airborne noise and that can minimize the potential for relative motion between the patient and the transducer mechanism and, therefore, minimize the amount of surface motion noise that may generated.

Sometimes it is desirable to either continually or periodically monitor a patient's body sounds at a specific location on the patient's body. Continual holding of the stethoscope head at the specific location can be burdensome for a doctor, nurse, or technician to do. Returning to the exact location at periodic intervals may also be difficult. A further object of the present invention, therefore, is to provide an interface device that can be used to establish a good reference point for continual or periodic body signal monitoring.

SUMMARY OF THE INVENTION

The present invention provides a patient-to-transducer interface device for use in holding a transducer such as a stethoscope head against the surface of a living body. The interface device comprises a flange having a substantially bell torus shape with an outer flat section and an inner raised section. A substantially centrally-located through hole passes through the flange for receiving the transducer or stethoscope head. The flange further has a channel positioned in the inner raised section outward from the central through hole.

The channel essentially encircles the through hole and has an opening on the bottom side of the flange. A soft pliable pack is received in the channel such that a portion of the pack partially protrudes from the opening of the channel. Preferably, the pack comprises a silicone gel material. A seal having a through hole is positioned in the central through hole of the flange. The seal has an uneven inner surface that preferably has a substantially sawtooth configuration.

An adhesive material is applied to the bottom side of the flange outward from the channel. The adhesive material aids in holding the interface device on the skin surface of a patient. Once the interface device is applied to the skin surface, the transducer or stethoscope head may be inserted through the through hole and pressed against the skin surface.

BRIEF DESCRIPTION OF THE DRAWINGS

The above and other objects and advantages of the invention will become apparent from consideration of the following detailed description when read in conjunction with the accompanying drawings, in which like reference characters refer to like parts throughout. The terms "upper", "lower", "top" and "bottom" may be used throughout the specification for purposes of clarity and convenience in describing the invention. The use of such terms is not intended to be limiting with regard to any particular orientation of the device.

DETAILED DESCRIPTION OF THE INVENTION

Figure 1:
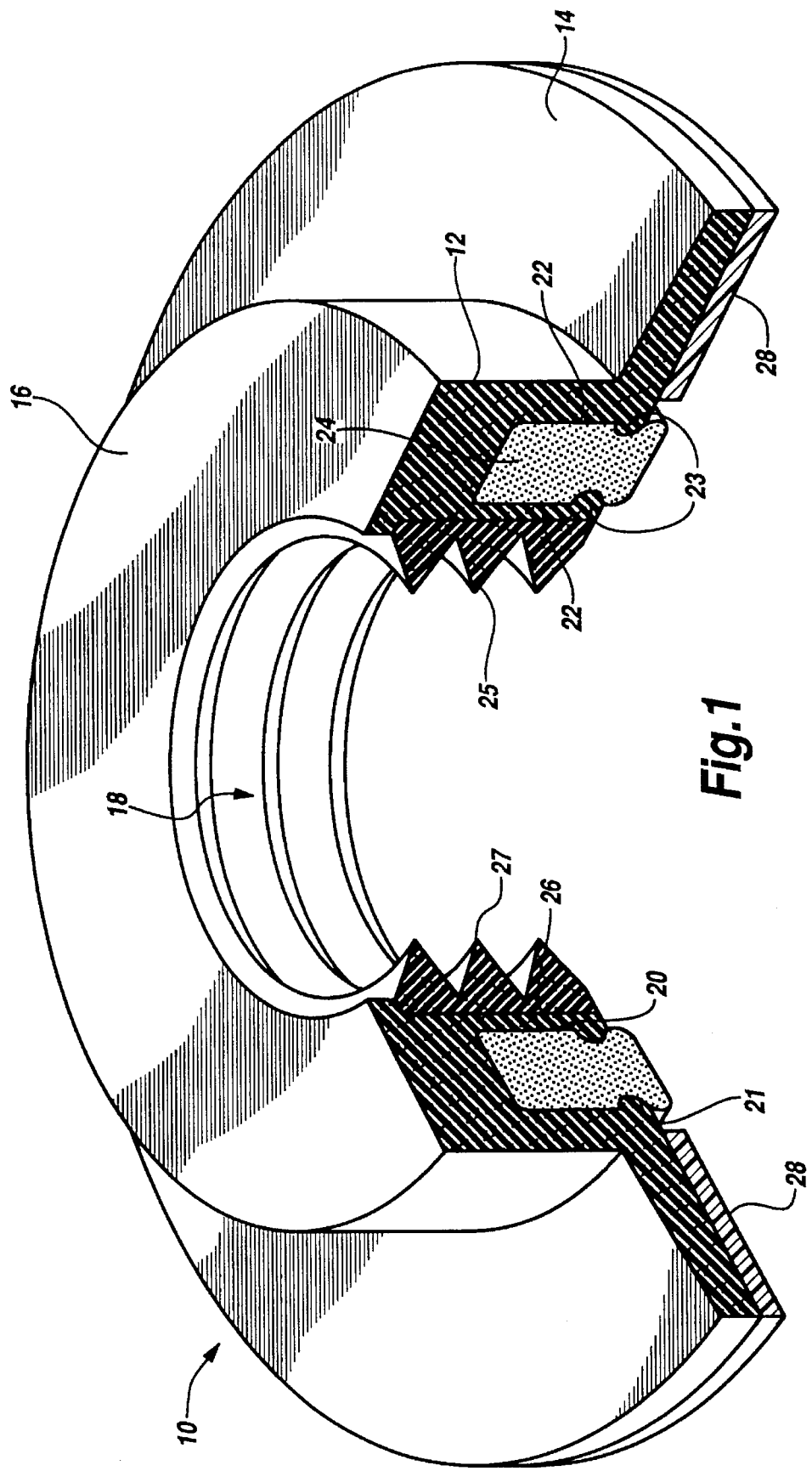
FIG. 1 is perspective cutaway view of a patient-to-transducer interface device.
Figure 2:
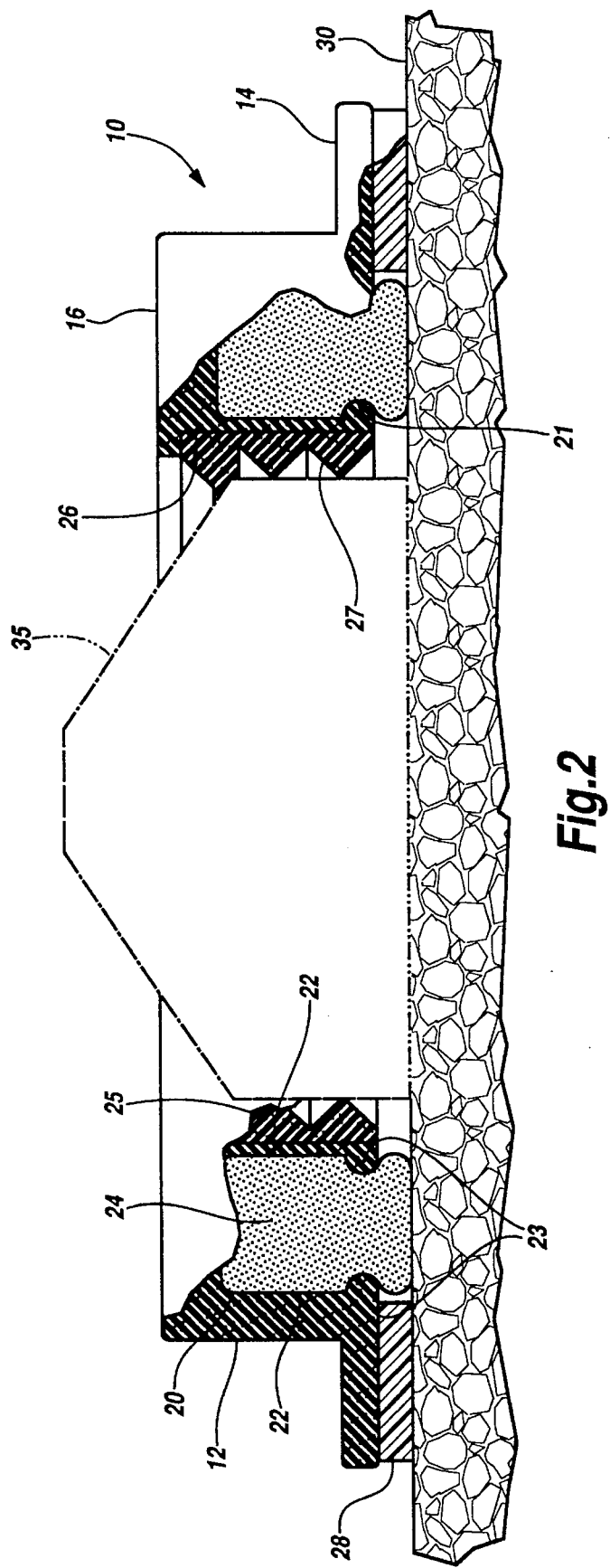
FIG. 2 is a side cross-sectional view of the interface device of FIG. 1 and a stethoscope head in engagement with the skin surface of a patient.

With reference to FIGS. 1 and 2, the present invention provides a disposable patient-to-transducer interface device 10 that may be used to securely hold a transducer 35 such as a stethoscope head 35 positioned against the skin surface 30 of a patient. As shown in FIG. 2 and explained in further detail below, the interface device 10 may be adhered to the patient's skin surface 30 and the stethoscope head 35 securely received in an opening provided in the device 10.

When in use, the interface device 10 substantially surrounds the stethoscope head 35 thereby providing a passive barrier to the airborne noise. The interface device 10 also develops a relatively good air seal around the stethoscope head 35 and thus provides an additional barrier to the airborne noise. Furthermore, the interface device 10 prevents substantial movement of the transducer 35 and, thereby, minimizes the amount of surface motion noise generated and detected by the transducer 35. In addition, when the interface device 10 is attached to the skin surface of the patient as shown in FIG. 2, it establishes a good reference point whereby continual or periodic monitoring of a particular location on the patient may be accomplished.

The interface device 10 comprises an outer flange or housing 12 that is generally in the shape of a bell torus having a flat outer circular section 14 and a raised inner circular section 16. The flange 12 also has a central circular through hole 18 that receives the stethoscope head 35. The through hole 18 preferably has a shape that substantially follows the contour of a portion of the outer surface of the stethoscope head 35. Typically, the contour of the outer perimeter of a stethoscope head is circular. Preferably, the flange 12 is made substantially from an elastomer material such as rubber. The material is preferably relatively firm, so that the bell torus shape of the flange 12 may be maintained, yet also relatively flexible so that the interface device 10 can flex and deform and, therefore, effectively be adhered to skin surfaces of varying contour and softness.

The raised inner section 16 of the flange 12 is provided with a channel 20 that has an opening 21 to the bottom of the flange 12. The channel 20 extends about the inner section 16 of the flange 12 in a circular manner when viewed from the bottom of the flange 12. As shown in FIGS. 1 and 2, the channel 20 is generally rectangular in cross-section. Near the opening 21 of the channel 20, however, on opposite sides 22 of the channel 20 are inwardly-extending projections 23. As discussed further below, the projections 23 help to hold a relatively soft pliable pack 24 within the channel 20.

The channel 20 is filled with a soft pliable pack 24 that can be easily deformed to conform to the skin surface 30 of a patient. Whereas the flange 12 is also preferably made from a material that is relatively soft so as to be also be able to conform to the skin surface 30 of a patient, the soft pack 24 is preferably made from a material that is even softer and more easily deformed. The soft pliable pack 24 may comprise a flexible outer sheath or bag that is filled with a soft material or composite of soft materials. An outer sheath or bag, however, is not required, and the pack, therefore, can merely comprise a soft material or composite of materials.

In a preferred embodiment, the soft pliable pack 24 comprises an outer sheath that is filled with a gel material such as silicone gel. The sheath of bag may alternatively be filled with a soft foam or a liquid. Or, the soft pack 24 may comprise a soft sponge or foam that may or may not be held in a flexible sheath or bag. Preferably, the soft pack 24 has a hardness that measures near the lower end of the Durometer Shore A scale. For example, a soft foam measuring in the range of 10–15 Shore A may be suitable. The flange 12, therefore, preferably would be made from a material that is higher on the Durometer Shore A scale.

The soft pliable pack 24 is generally in the shape of a torus and, as shown in FIGS. 1 and 2, is squeezed into the channel 20 so that part of the pack 24 protrudes outside the channel 20. The side projections 23 help keep a majority of the soft pack 24 within the channel 20. When the interface device 10 is attached to the patient's skin surface 30, the soft pack 24 is flattened and deformed by the skin surface 30 forming a comfortable and positive air seal.

A generally circular seal 25 made substantially from a relatively soft elastomer material is affixed to the inner surface 26 of the flange 12 that surrounds the through hole 18. The seal 25 preferably has an uneven inner surface 27 such as a modified labyrinth or sawtooth configuration that aids in holding the transducer 35 in place. The seal 25 with its inner surface 27 effectively grasps the stethoscope head 35 forming an effective air seal between the stethoscope head 35 and the flange 12. Preferably, the seal 25 is made from a rubber or plastic material that is harder than the flange material. The seal 25 should, however, be soft enough to slightly deform and form a good seal around the stethoscope head 35 when the stethoscope head 35 is inserted into the device 10. Although the seal 25 is described as a separate element from the flange 12, it may also be an integral part of the flange 12. In such a case, the through hole 18 would be provided with the uneven surface.

Preferably, the flange 12, soft pliable pack 24, and seal 25 are made of materials of different softness with the pliable pack 24 being the softest and most easily deformed and the seal 25 being the hardest and least deformable. With the different softness levels of the various components 12, 24, and 25, different impedance levels against different sound frequencies can be obtained. Softer materials tend to resist the higher frequencies whereas harder materials tend to resist the lower frequencies. As sound is transmitted through the interface device 10 to the transducer 35, it passes through the flange 12 where certain frequencies are impeded. As the sound continues to travel and passes through the soft pliable pack 24, higher frequencies are impeded. Lower frequencies are impeded as the sound passes through the seal 25. The variation in the types of frequencies that are impeded provides a better overall barrier to sound.

Secured to the underside of the flat section 14 of the flange 12 is adhesive tape 28 that is used to hold the interface 10 against the patient's skin. Preferably, the adhesive tape is covered with a nonadhesive layer or sheet that is removed before the flange 12 is applied to a patient. Other suitable adhesive materials other than tapes may also be employed. The adhesive material, however, preferably forms a relatively strong bond but one that can be easily broken in order to safely remove the interface device 10 from the patient.

When in use, the interface device 10 is applied to the patient's skin 30 by pressing the flat section 14 with the adhesive tape 28 against the skin 30. As the pressure is applied, the portion of the soft pack 24 that protrudes outside of the channel 20 will be slightly flattened and squeezed forming a good air seal around the lower end of the central through hole 18. The adhesive tape 28 holds the interface device 10 securely in position against the patient. The stethoscope head 35 may then be inserted into the through hole 28 and pressed against the patient's skin surface 30. The seal 25 effectively grasps the stethoscope head 35 preventing substantial movement of the head 35 and providing a good air seal.

Where continual monitoring of the patient is desired, the interface device 10 can be used to maintain the stethoscope head 35 in a proper position for an indefinite time. Furthermore, where periodic monitoring of a specific location of the patient is desirable, the interface device 10 can be applied to the specific location and the stethoscope head 35 inserted and removed from the device 10 as needed to take periodic readings of the patient's body sounds.

While a single embodiment of the invention has been shown and described, it should be recognized that other variations, substitutions, or modifications will occur to those skilled in the art. Any such variations, substitutions, and modification are intended to fall within the scope of the invention as defined in the appended claims. For example, the interface device has been described as having a generally circular configuration; however, the shape of the device, and in particular the shape of the through hole 18, can vary depending upon the shape of the transducer mechanism or stethoscope head that is to be used.

What is claimed is:

1. A patient-to-transducer interface device for use in holding a transducer against the surface of a body, said interface device comprising:

a flange having first and second sides, a through hole passing through said flange from said first side to said second side, and a channel positioned outward from said through hole, said channel having an opening on said second side of said flange;

a pliable pack positioned in said channel, wherein said pliable pack is softer than said flange; and adhesive material applied to said second side of said flange outward from said channel.

2. A patient-to-transducer interface device according to claim 1, wherein said flange has a generally bell torus shape with a substantially flat outer section and inner raised section.

3. A patient-to-transducer interface device according to claim 2, wherein said through hole of said flange is located in said inner raised section of said flange such that said inner raised section substantially encircles said through hole.

4. A patient-to-transducer interface device according to claim 3, wherein said channel substantially encircles said through hole and said pliable pack partially protrudes from said opening of said channel.

5. A patient-to-transducer interface device according to claim 1, further comprising a seal positioned within said through hole.

6. A patient-to-transducer interface device according to claim 5 wherein said seal is harder than said flange.

7. A patient-to-transducer interface device according to claim 5, wherein said seal is substantially in the shape of a collar with an uneven inner surface.

8. A patient-to-transducer interface device according to claim 7, wherein said uneven inner surface of said seal has a substantially sawtooth configuration.

9. A patient-to-transducer interface device according to claim 1, wherein said pliable pack comprises a silicone gel material.

10. A patient-to-transducer interface device according to claim 1, wherein said pliable pack comprises a soft sponge material.

11. A patient-to-transducer interface device according to claim 1, wherein said pliable pack comprises a soft foam material.

12. A patient-to-transducer interface device according to claim 1, wherein said pliable pack partially protrudes from said opening of said channel.

13. A patient-to-transducer interface device according to claim 1, wherein said flange comprise an elastomer material.

14. A patient-to-transducer interface device according to claim 1, wherein said flange has an inner surface that defines said through hole and said inner surface has an uneven contour.

15. A patient-to-transducer interface device for use in holding a transducer against the surface of a body, said interface device comprising:

a flange having a substantially bell torus shape with an outer flat section, an inner raised section, and a through hole that is substantially surrounded by said inner raised section, said flange further having a channel positioned outward from said through hole in said inner raised section, said channel having an opening on one side of said flange;

a soft pliable pack received in said channel and partially protruding from said opening of said channel, wherein said pliable pack is softer than said flange;

a seal having a through hole positioned in said through hole of said flange; and adhesive material applied to said one side of said flange outward from said channel.

16. A patient-to-transducer interface device according to claim 15, wherein said channel extends around said through hole of said flange.

17. A patient-to-transducer interface device according to claim 15, wherein said seal is substantially in the shape of a collar with an uneven inner surface.

18. A patient-to-transducer interface device according to claim 17, wherein said uneven inner surface of said seal has a substantially sawtooth configuration.

19. A patient-to-transducer interface device according to claim 15, wherein said soft flexible pack comprises a silicone gel material.

* * * * *